United States Patent [19]

Esau

[11] Patent Number: Plant 5,382

[45] Date of Patent: Jan. 1, 1985

[54] ALMOND TREE 'SR100'

[76] Inventor: Raymond J. Esau, 7860 Sunset Dr., Atwater, Calif. 95301

[21] Appl. No.: 451,554

[22] Filed: Dec. 20, 1982

[51] Int. Cl.[3] ..... A01H 5/00
[52] U.S. Cl. ..... Plt./30
[58] Field of Search ..... Plt./30

*Primary Examiner*—James R. Feyrer
*Attorney, Agent, or Firm*—Roger B. Webster

[57] ABSTRACT

An almond tree which is medium size, open, spreading, and vigorous; abundantly foliated with medium size, acuminate, acutely pointed leaves having a glandular, coarsely serrate margin, a medium length petiole, and medium size, alternate, globose, green glands; blooms very heavily with reddish-pink flowers; and is a regular and heavy bearer of well-distributed nuts borne in thin, tough hulls; the out-of-hull nuts and the out-of-shell kernels being of medium size and oval form.

1 Drawing Figure

BACKGROUND OF THE VARIETY

Field of the Invention

As an agriculturist, and attendant the operation and maintenance of my ranch located near Atwater, Merced County, Calif., I frequent such ranch for the purpose of inspection, soil preparation for planting, cultivation, and irrigation, and—against the background of the such activities—the present variety of almond tree was discovered.

CLASSIFICATION OF THE VARIETY

The present new and distinct variety of almond tree is embraced by Class 30, Plants, of the U.S. Patent Office Manual of Classification.

PRIOR VARIETIES

Among the existent varieties of almond trees which are known to me, and mentioned herein, is Nonpareil (unpatented).

ORIGIN OF THE VARIETY

During the course of soil preparation for planting of an orchard, the present variety of almond tree was discovered by me on my ranch (located as aforementioned) growing as a chance seedling near a fence line on such ranch. Upon observing certain new and distinct characteristics of such chance seedling, and continuing to maintain it under close and careful observation, I confirmed the novelty thereof and determined to asexually reproduce it as a potential commercial variety.

ASEXUAL REPRODUCTION OF THE VARIETY

The present variety of almond tree was asexually reproduced—on my behalf and by a commercial nursery—by budding, and—in maturity—such reproduction ran true to the original tree (chance seedling) in all respects.

SUMMARY OF THE VARIETY

The present variety of almond tree is, characteristically, medium size, open, spreading, and vigorous; abundantly foliated with medium size, acuminate, acutely pointed leaves having a glandular, coarsely serrate margin, a medium length petiole, and medium size, alternate, globose, green glands; blooms very heavily with reddish-pink flowers; and is a regular and heavy bearer of well-distributed nuts borne in thin, tough hulls; the out-of-hull nuts and the out-of-shell kernels being of medium size and oval form.

The present variety of almond tree is further characterized:

By blooming, very heavily, with the Nonpareil, but harvesting later—desirably permitting of separate harvesting operations. The very heavy bloom carries well into the blooming period of later-blooming varieties, and which enhances pollination.

By medium size, oval nuts which hang well on the tree, with very little pre-harvest dropping, yet require very little tree shaking to substantially clean the tree of the entire crop—this being not only economically advantageous, but also minimizes carry-over of pests to the next crop season.

By nuts which remain well in the hull during harvest and which nut-in-hull retention is advantageous to non-tillage orchard operations such as mechanical sweeping, and pick-up from the ground, or from a cover crop, after shaking, and By nuts which have a good flavor and appearance, and are easily blanched.

BRIEF DESCRIPTION OF THE DRAWING

The drawing is an illustration, by photographic reproduction in color, of twigs with in-hull nuts; and, separately, in-hull nuts, nuts out of hull, and kernels out of shell.

DESCRIPTION OF THE VARIETY

The botanical details of this new and distinct variety of almond tree—with color definitions (except those in common color terms) referenced to Maerz and Paul Dictionary of Color (First Edition)—are as follows:

TREE

Density: Open.
Size: Medium.
Vigor: Vigorous.

TRUNK

Size: Medium.
Texture: Smooth.

BRANCHES

Size: Medium.

Texture: Smooth.
Lenticels: Medium number. Medium size.
Branching habit: Spreading.
Color:
*New wood.*—Gray.
*Mature wood.*—Dull.

FOLIAGE

Quantity: Abundant.

LEAVES

Size: Medium.
*Average length.*—$3\frac{5}{8}''$.
*Average width.*—$1\frac{3}{8}''$.
Shape: Acuminate. Acutely pointed.
Thickness: Thin.
Texture: Smooth.
Margin: Glandular. Coarsely serrate.
Petiole: Medium length. Medium thickness.
Glands: Average number — 2; Alternate; Medium size; Globose; Green; Positioned on petiole.
Stipules: On petiole.
Color:
*Top side.*—Medium green (23-L-8).
*Under side.*—Lighter green (22-L-8).

BLOOM

Amount of bloom: Very heavy.
Color: Reddish pink.
Blooming period: Medium. Feb. 22nd–Mar. 15th. Blooms with Nonpareil.

CROP

Bearing: Regular bearer.
Productivity: Heavy.
Distribution of nuts on tree: Well distributed.
Harvest period: Sept. 25th.–Oct. 5th. Later than Nonpareil.
Tenacity: Hangs well on tree. Easy to harvest. Easy to hull.

HULL

Outer surface: Smooth.
Form: Regular.
Thickness: Thin.
Flesh: Tough.
Suture: Flat depressed.
Color: Green (20-K-4) without silvery sheen.
Dehiscence: Opens freely.
Splitting: Along suture.

NUT

Size: Medium.
*Average length.*—1 11/32".
*Average width.*—13/16".
*Average thickness.*—$\frac{3}{4}''$.
*Average weight.*—1/10 oz.

Form:
*Length/width.*—Oval.
*Width/thickness.*—Medium.
Shell: Soft. Thick. Smooth.
*Outer shell.*—Crumbling. Adheres to hull.
*Inner shell.*—Hard. Well sealed.
Color: Brown (12-K-7).
Pits: Small. Numerous. Deep. Irregular.
Base: Square.
Stem scar: Large.
Apex: Obtuse; Acuminate; Shouldered; Tip recurved.
Wing: Narrow; Thin; Tapered toward apex.
Inner surface: Dark colored.
Ventral streak: Dark; Narrow; Long; Point acute.
Percentage of kernel to nut: 60.5%.

KERNEL

Size: Medium.
*Average length.*—15/16".
*Average width.*—9/16".
*Average thickness.*—$\frac{3}{8}''$.
*Average weight.*—1.49 Grams per kernel.
Form
*Length/width.*—Oval.
*Width/thickness.*—Medium.
Base: Ventrally oblique.
Stem scar: Large; Obtuse.
Apex: Acute; Acuminate; Shouldered; Tip recurved.
Texture: Smooth; Furrowed.
Pellicle: Thin.
Pubescence: Smooth; Veined.
Color: Medium brown (13-K-8).
Number of doubles: Few.
Defective kernels: Gummy — few.
Flavor: Normal.
Quality: Good.

RESISTANCE TO INSECTS AND DISEASES

No unusual susceptibilities noted. Substantial resistance to worms.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, which blooms very heavily with reddish-pink flowers, the bloom being with the Nonpareil, and which tree is a regular and heavy bearer of medium size, oval nuts in harvest after the Nonpareil; the nuts having a minimum of pre-season drop yet shake easily and cleanly from the tree, and having good nut-in-hull retention for harvest.

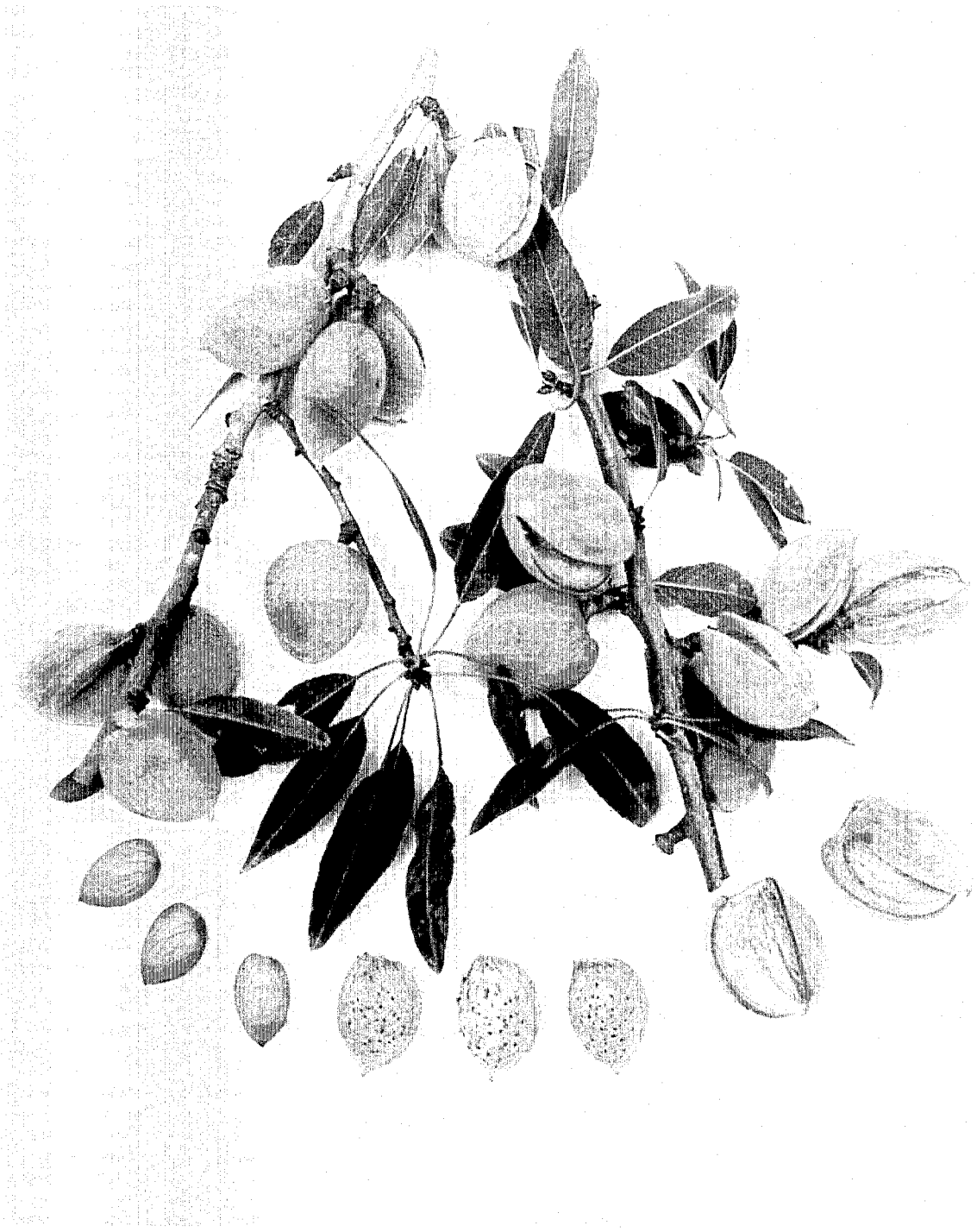

* * * * *